(12) United States Patent
Brod

(10) Patent No.: US 6,346,243 B1
(45) Date of Patent: Feb. 12, 2002

(54) INHIBITION OF TRANSPLANT REJECTION BY TYPE ONE INTERFERON

(75) Inventor: Staley A. Brod, Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/314,503

(22) Filed: May 19, 1999

Related U.S. Application Data

(63) Continuation-in-part of application No. 08/946,710, filed on Oct. 8, 1997, which is a continuation-in-part of application No. 08/844,731, filed on Apr. 21, 1997, which is a continuation-in-part of application No. 08/631,470, filed on Apr. 12, 1996, which is a continuation-in-part of application No. 08/408,271, filed on Mar. 24, 1995, now abandoned, which is a continuation-in-part of application No. 08/226,631, filed on Apr. 12, 1994, now abandoned.

(51) Int. Cl.[7] ............................................. A61K 38/21
(52) U.S. Cl. .................... 424/85.4; 424/85.6; 424/85.7
(58) Field of Search ............................. 424/85.4, 85.6, 424/85.7

(56) References Cited

PUBLICATIONS

Nagler et al. Blood 89(11):3951–9, 1997.*

* cited by examiner

*Primary Examiner*—David Saunders
*Assistant Examiner*—Amy DeCloux
(74) *Attorney, Agent, or Firm*—Benjamin Aaron Adler

(57) ABSTRACT

The present invention provides a method of using a convenient, oral administered and non-toxic immunomodulating agent to suppress transplant rejection. Such agent is a type one interferon.

8 Claims, 5 Drawing Sheets

INHIBITION OF TRANSPLANT REJECTION BY TYPE ONE INTERFERON

CROSS-REFERENCE TO RELATED APPLICATION

This application is a continuation-in-part of application Ser. No. 08/946,710, filed Oct. 8, 1997, which was a continuation-in-part of application Ser. No. 08/844,731, filed Apr. 21, 1997, which was a continuation-in-part of application Ser. No. 08/631,470, filed Apr. 12, 1996, which was a continuation-in-part of application Ser. No. 08/408,271, filed Mar. 24, 1995, now abandoned, which was a continuation-in-part of application Ser. No. 08/226,631, filed Apr. 12, 1994, now abandoned.

BACKGROUND OF THE INVENTION

1. Field of the Invention

The present invention relates generally to the fields of neurology, immunology and protein chemistry. More specifically, the present invention relates to uses of oral Type I interferons to inhibit transplant rejection.

2. Description of the Related Art

Type I diabetes is a chronic disorder that results from autoimmune destruction of the insulin-producing pancreatic β cell. In the United States, the prevalence of type I diabetes by age 20 years is 0.26% and lifetime prevalence approaches 0.40%; thus approximately 1.5 million Americans have type I diabetes [1]. Once type I diabetes patients become insulin dependent, there is little therapeutic options except insulin replacement.

The Relevance of the NOD Mouse Model to Diabetes Mellitus:

The NOD mouse is a model of the human autoimmune disease type I diabetes [2–4]. The NOD mouse model is presumed to be T cell subset mediated and dependent on inflammatory cytokines for disease expression. Many key features of human type I diabetes are reflected in the NOD mouse: the development of insulinitis with infiltration of lymphocytes into the pancreatic islets of Langerhans that are selectively cytotoxic to the insulin producing β cells; the dependence of disease pathogenesis by T cells; and transmission of type I diabetes by hematopoietic cells in bone marrow [5–9].

Immunoregulatory Cytokine Imbalances in Type I Diabetes:

Destruction of islet cells in NOD mice has been associated with a subset of T cells producing IFN-γ [17]. IFN-γ has been detected in lymphocytes infiltrating islets of human subjects with recent onset type I diabetes [18] and antibodies against IFN-γ protect against diabetes development in NOD mice [19, 20] and BB rats [21]. IFN-γ transgenic mice develop type I diabetes with inflammatory destruction of the islets [22, 23]. The incidence of type I diabetes correlates with IFN-γ-producing islet T cells in NOD [24] and in NOD.scid mice [25]. This suggests that intraislet IFN-γ may be critical in the development of diabetes mellitus (DM).

IFN-α has been detected in β cells of animals and human subjects with recent onset type I diabetes [26, 27] and may elicit an immune mediated destruction of β cells; anti-IFN-α antibody prevents this β cell damage [28]. Islet expression of IFN-α, induced by polyinosinic-polycytidylic acid {poly (I:C)} or expressed from a transgene, precedes diabetes in both the BB rat and streptozotocin (STZ)-treated mice [29]. However, IFNs are well known to have dose related opposing effects on immune responses. In contrast to the results above, poly (I:C) can protect against overt type I diabetes in the NOD mouse [30] and can prevent the development of diabetes in BB rats by interfering with the development of insulitis [31]. Parenteral IFN-α can decrease the development of spontaneous diabetes, the passive transfer of diabetes in NOD mice and decrease islet inflammation [32]. Therefore, IFN-α is not intrinsically diabetogenic and may be protective. Indeed, moderate amounts of intraislet IFN-α may be anti-inflammatory.

IL-4 and IL-10 cytokines can protect against the development of type I diabetes in the NOD mouse [33]. Transgenic NOD-IL-4 and rIL-4 administration to prediabetic NOD mice is protective against type I diabetes [34, 35], whereas the impairment of IL-4 production by PBMC or T cells was found in type I diabetes patients at diabetes onset [36]. IL-10 delays the onset of disease and reduces the incidence of diabetes, the severity of insulitis, prevents cellular infiltration of islet cells, and promotes normal insulin production by β cells [37, 38].

Adoptive Transfer of Protection Against Allograft Islet Rejection:

CD8+ cytotoxic T cell lines and clones generated from lymphocytic islet infiltrates can transfer diabetes rapidly without CD4+ T cells [42]. Islet-infiltrating lymphocytes from prediabetic SCD mice rapidly transfer diabetes to NOD.scid mice; cotransfer of splenocytes or CD4+, but not CD8+ spleen cells, together with islet infiltrating lymphocytes from prediabetics delayed the rapid transfer of type I diabetes, suggesting CD4+ cells also mediate immunoregulation [43, 44]. CD4+ T cell clones from unprimed NOD mice can protect against adoptive transfer of DM [45].

The effect of pro-inflammatory (IL-1, IL-2, IL-6, TNF-α, type II IFN IFN-γ) and anti-inflammatory (IL-4, IL-10, IFN-α) cytokines in experimental models of allograft islet transplantation has been investigated. Enhanced expression of pro-inflammatory type II IFN-γ contribute to graft destruction [48]. Pro-inflammatory cytokines IL-1β, TNF-α, and IFN-γ are cytotoxic to human islet 0-cells in vitro [49]. Non-function of isologous and allogeneic islet grafts is prevented by treatment with or increased IL-4 and IL-10 and decreased type II IFN IFN-γ [33, 50]. Inhibition of NF-κB suppresses immune-mediated cell death in β-cells and protects from diabetogenic T cell immune attack in vivo. Therefore, increased IL-4/IL-10, inhibition of IFN-γ and NF-κB activation may protect pancreatic β-cells [51].

Rejecting islet allografts contain a mixture of pro-inflammatory and anti-inflammatory cytokines such as IL-2 and IFN-γ mRNA transcripts [52] and increased expression of IL-2, IL-4, TNF-α, IFN-γ and IL-10 mRNAs at the peak of the cellular infiltrate (on day 5) in islet allografts [53]. Allogeneic islet grafts showed increased IL-1 from 1 to 7 days, IL-2 and IFN-γ transcripts at 1, 3, 5, and 7 days with a peak at day 5, IL-6 expression at 1 day, with constant IL-10 at all time points [54]. ICAM-1 antisense oligonucleotides can decrease increased IL-1 mRNA expression following kidney capsule islet transplantation and prolong allograft islet survival [55]. However, the simple Th1 to Th2 immune deviation does not blunt the severity of MHC-mismatched allograft rejection [50].

Type I Interferons:

In 1957 Isaacs and Lindenmann described a factor (interferon) produced by virus infected cells with rapid antiviral activity [57]. Type I IFNs are composed of two highly homologous proteins IFN-α (leucocyte IFN) and IFN-β (fibroblast IFN) with similar biological properties [58], interact with the same cell receptor [59], and resist stomach acidity. Fifty to two hundred high affinity type I receptors are found on all lymphoid cells, including the gut associated lymphoid tissue (GALT) [60–62]. Therefore, type I IFNs are immunoactive endogenously produced proteins that can be active in the gut. Systemic effects may be achieved with IFN-β administered directly to the upper GI tract in experimental animal models of auto-immune disease and human auto-immune disease [63, 64] and does not result in detectable levels of IFN-α in the blood [65–68] nor β$_2$-microglobulin, neopterin, or 2–5A synthetase protein arkers of IFN absorption [69].

GALT (Gut Associated Lymphoid Tissue):

The afferent gut-associated lymphoid tissue has multiple types of constituent immune cells in lymphoid nodules termed Peyer's patches (PP) [78]. Peyer's patches contain T lymphocytes that are predominantly composed of the CD14+ T cells [79, 80] where regulatory cells can be generated [81, 82]. GALT activated lymphocytes, by virtue of their ability to circulate through the body, potentially can transfer their biological activities widely in the absence of circulating cytokines after contacting type I IFN in the gut-associated lymphoid tissue [83–87]. At their destination (islets), type I IFN-activated cells may release anti-inflammatory type I IFNs which are able to inhibit neighboring inflammatory cells by paracrine cytokine release.

Islet transplantation:

Islet transplants possess significantly potential advantages over whole-gland transplants because it is a simple procedure with only small risk, may achieve insulin-independence [88], has clear advantages over exogenous insulin therapy but limited success to date [89]. However, type I diabetes is characterized by the presence of an autoimmune memory. This recurrence of autoimmunity is partly responsible for the need of extensive immunosuppression in islet transplantation in type I diabetes [90].

The effect of pro-inflammatory and anti-inflammatory cytokines in experimental models of allograft islet transplantation has been investigated. Enhanced expression of pro-inflammatory Type II IFN-γ contribute to graft destruction [48]. Rejection of isologous and allogeneic islet grafts is prevented by treatment with or increased IL-4 and IL-10 and decreased type II IFN-γ [33, 50]. Inhibition of NF-κKB suppresses immune-mediated cell death in β-cells and protects from diabetogenic T cell immune attack in vivo. Therefore, increased IL-4/IL-10 and inhibition of NF-κB may protect pancreatic β-cells [51].

Currently used immunosuppressant agents are either toxic or cannot prevent the spontaneous onset of DM. Cyclosporine, prednisone, azathioprine, and FK506 are toxic to islet cells [91–96]. 15-deoxyspergualin prolongs allograft islet survival, but high doses do not prevent rejection indefinitely and are toxic [97, 98]. Leflunomide has no apparent toxicities in mice, but does not significantly reduced the incidence of spontaneous diabetes in NOD mice, in distinct contrast to ingested murine IFN-α [99]. Oral mycophenolate mofetil, an antiproliferative agent, does not prevent allograft rejection at day +30 [100] and does not block islet graft rejection in spontaneously diabetic BB rats [101]. In pig islet allografts, a combination of cyclosporine, azathioprine, and prednisolone, 15-deoxyspergualin, and antithymocyte globulin was successful. However, this immunosuppressive protocol resulted in a high rate of infectious complications [94].

The prior art is deficient in the lack of effective means to treat transplant rejection by using oral type I interferons. The present invention fulfills this long-standing need and desire in the art.

SUMMARY OF THE INVENTION

The present invention is directed to a non-toxic method to treat or even prevent organ transplant rejection by using oral type I interferons. In one embodiment of the present invention, there is provided a method of treating transplant rejection in an animal by orally administering a type one interferon, wherein the type one interferon is ingested after oral administration. Preferably, the type one interferon is alpha-interferon or beta-interferon. More preferably, the interferon is selected from the group consisting of human recombinant interferon, rat interferon and murine interferon.

In another embodiment of the present invention, there is provided a method of preventing transplant rejection in an animal by orally administering a type one interferon, wherein the type one interferon is ingested after oral administration.

In another embodiment of the present invention, there is provided a method of preventing transplant rejection in an animal, comprising the step of administering a type one interferon to said animal.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
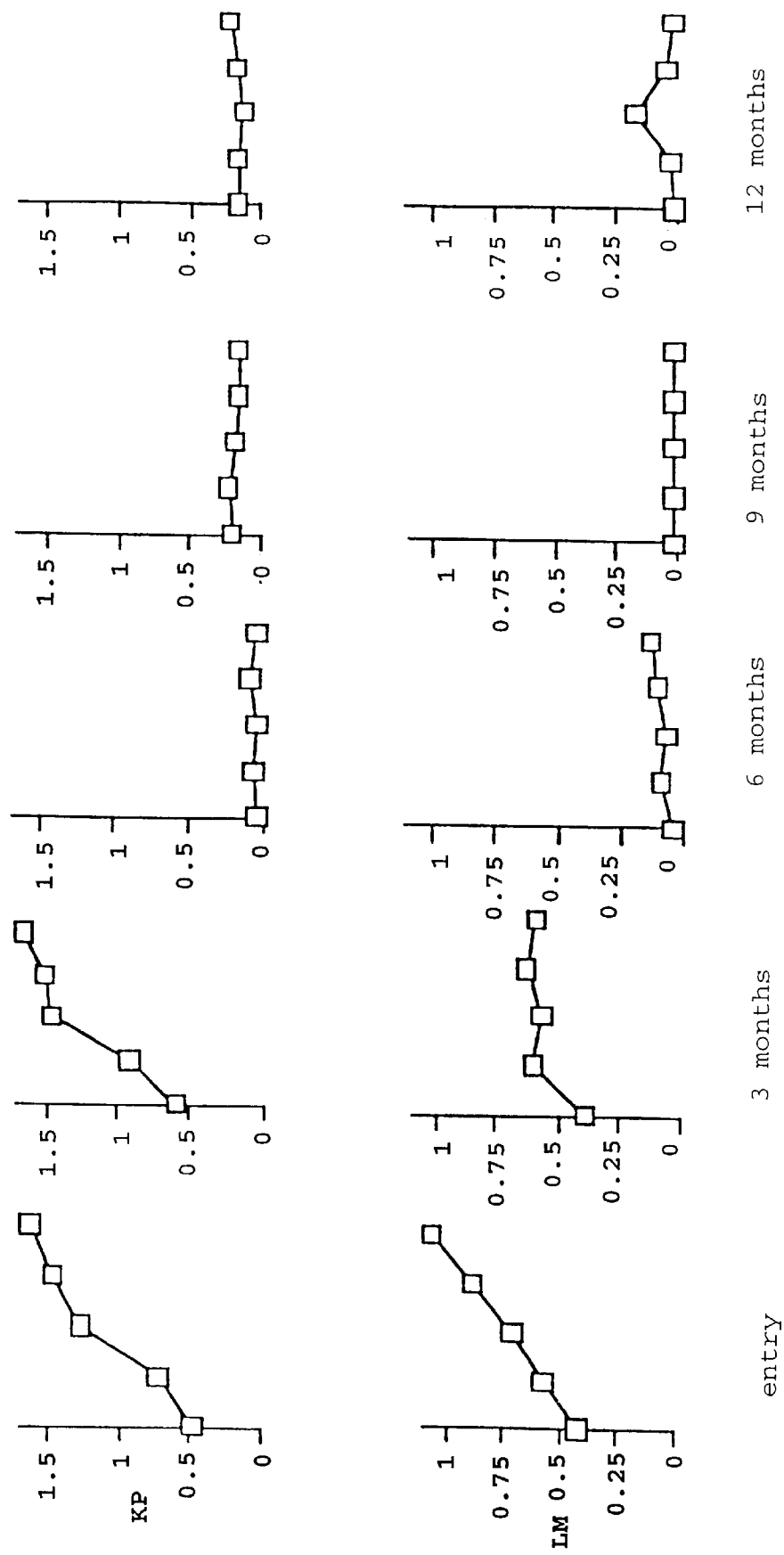
FIGS. 1A and 1B show that every other day ingested IFN-A prolongs the "honeymoon" period in newly diagnosed IDDM.

The present invention examines applicability of ingested IFN-α in an animal transplant model with anatomic and physiological similarities to human. The natural history of type I diabetes development after adoptive transfer in NOD-.scid mice is predictable and interventional studies in the NOD.scid mouse can be designed such that treatment is initiated at a pre-symptomatic stage prior to the occurrence of overt diabetes (e.g., 5–7 weeks) and after the start of disease (e.g., 8–9 weeks). It was previously shown that ingested type I IFN inhibits chronic relapsing experimental autoimmune encephalomyelitis (CR-EAE), inhibits the adoptive transfer of EAE by T cells, decreases both antigen-specific and mitogen-induced pro-inflammatory cytokine secretion in EAE [10–15].

The present invention determines whether ingested murine IFN-α (mIFN-α) administered to NOD mice inhibits insulinitis and suppresses type I diabetes. Daily ingested mIFN-α decreased islet inflammation and suppressed diabetes. Ingestion of mIFN-α increased the Con A and ionomycin/PMA-induced production of IL-4, IL-10 and IFN-β secretion in spleen cells from treated mice. Adoptive transfer of unstimulated splenocytes secreting IL-4 and IL-10 from mIFN-α fed donors suppresses spontaneous DM in recipients. The protective effect of adoptively transferred unstimulated splenocytes demonstrates the presence of ingested IFN-α-activated regulatory splenic cell populations that may work via increased IL-4 or IL-10 production. Ingested IFN-α may potentially provide a continuous, convenient, non-toxic and effective therapy for type I diabetes administered during vulnerable periods in at-risk populations [16].

Recently, it was demonstrated that ingested IFN-α has therapeutic potential in newly diagnosed type I diabetes. Because type I diabetes is a chronic disorder that presumably results from autoimmune destruction of the insulin-producing pancreatic β cells, the therapeutic potential of interventions in type I diabetes can be assessed in newly diagnosed patients. Since there is an historical experience of a low incidence of spontaneous remission in type I diabetes, interventions prolonging the "honeymoon" have been used as a positive outcome. Five patients with newly diagnosed IDDM were treated with ingested IFN-α within one month of diagnosis and examined baseline and Sustacal® induced C-peptide responses at 0, 3, 6, 9 and 12 months. Three of the five patients demonstrated biochemical "honeymoon" of at least a 30% increase of stimulated C-peptide levels at 0, 3, 6, 9 and 12 months after initiation of treatment. There were no discernible chemical or clinical toxicities associated with ingested IFN-α. The results demonstrate that ingested IFN-α can induce remission in recent onset type I diabetes and may prevent the onset of type I diabetes.

In order to examine the mechanism of transduction of a type I IFN signal across the gut wall, MxA message was examined in lymphocytes after ingestion of IFN-α. Mx is a type I IFN-specific induced mRNAlprotein indicating type I IFN/type I IFN receptor interaction [62] and is found in the absence of detectable serum IFN activity. MxA gene expression is a good marker for detecting minute quantities of biologically active type I IFN [70]. The relative levels of Mx mRNA signal was examined using semi-quantitative RT-PCR on splenocytes from mice and PMNC from man after IFN-α ingestion. Both mice and man demonstrated inducible levels of Mx mRNA after ingesting IFN-α. Murine spleen T cells and CD8+ T cells also demonstrated upregulation of Mx MnRNA. Murine whole spelnocytes demonstrated upregulation of Mx mRNA after IFN-α ingestion of 10 and 100 units, clinically effective doses, but not after 0, 1,000, or 5,000 units, clinically ineffective doses [14], demonstrating that ingested IFN-α acts via established pathways of type I IFN signaling [71]. The presence of MxA MRNA can demonstrate the rapid migration of immunoregulatory cells to sites of inflammation. The co-localization of MxA signal within hours of transfer and evidence for type I IFN upregulation of anti-inflammatory mediators in pancreas later may occur because MxA mRNA provides a marker for direct type I IFN/type I IFN receptor interaction on potential immunomodulatory cells [14, 71].

Because ingested type I IFNs have been shown to be biological response modifier (BRM) in EAE [10–12, 14] and the nOD mouse [16], it was determined whether ingested human recombinant IFN-α (Roferon) was non-toxic and was a biological response modifier in humans in a phase I clinical trial in multiple sclerosis (MS). IFN-α was dispensed in 5 cc aliquots of saline and immediately swallowed with 5–6 ounces of water on an empty stomach. In subjects with multiple sclerosis, a significant decrease in Con A-mediated proliferation and serum soluble intercellular adhesion molecule-1 (sICAM-1), a surrogate measure for disease activity in multiple sclerosis, was found after ingesting 10,000 and 30,000 units IFN-α. The multiple sclerosis subjects also showed decreased IL-2 secretion after ingesting 10,000 units IFN-α, and decreased IFN-γ, TGF-β and IL-10 production after ingesting 30,000 units IFN-α. These studies demonstrate that ingested IFN-α is a biological response modifier in humans with autoimmune disease [64].

The present invention demonstrates that no toxicity has been experienced [64] in all the current phase I and phase II trials involving ingested IFN-α. Daily ingested mIFN-α suppressed diabetes and adoptive transfer of unstimulated splenocytes from mIFN-α fed donors suppressed spontaneous DM in recipients [16]. Therefore, because the preliminary data suggests that ingested IFN-αmay be effective in the prevention of allograft rejection in mice, investigation of ingested IFN-α in clinically applicable large animal models is appropriate. Type I IFNs produce target organ-blind immunomodulation without respect to haplotypic background or sensitized antigen. A reductionistic approach to elucidate the underlying mechanism of ingested type I IFNs is critical. Because of its anatomical and physiological similarities to humans, the pig appears to be a suitable large animal model for preclinical studies of islet allograft transplantation in diabetes.

In one embodiment of the present invention, there is provided a method of treating transplant rejection in an animal by orally administering a type one interferon, wherein the type one interferon is ingested after oral administration. Preferably, the type one interferon is alpha-interferon or beta-interferon. More preferably, the interferon is selected from the group consisting of human recombinant interferon, rat interferon and murine interferon.

In a preferred embodiment, the type one interferon is administered in a dosage range of from about 50 I.U./kg to about 50,000 I.U./kg and can be administered either every day or every other day.

In another preferred embodiment, the animal can be mouse, pig, rat or human. An representative example of the transplant is islet allograft transplant.

The present invention is also directed to a method of preventing transplant rejection in an animal by orally administering a type one interferon, wherein the type one interferon is ingested after oral administration and administered continuously.

The following examples are given for the purpose of illustrating various embodiments of the invention and are not meant to limit the present invention in any fashion.

EXAMPLE 1

Diabetic Pigs Treated with Ingested IFN-α, do not Reject Islet Allograft Transplants.

Allogeneic islet from female Yorkshire donor pigs are used. Islet allograft recipients are Yucatan minipigs. Diabetes in recipients are induced by STZ. After DM is established in recipients, allogeneic islets are isolated from donor Yorkshire pigs and islets transferred into the portal vein or injected into the renal subcapsular area. Because there is no source for porcine type I IFNs, recipients are mock gavaged or gavaged with universal IFN-A/D, active on all mammalian cells, at 500 units/kg - 5,000 (100U/20 mg mouse is most effective dose in transplant mice, FIG. 2), 20,000, or 50,000 units/kg daily starting one week preceding STZ and treated daily thereafter. BS is checked to determine if rejection has occurred. Confirmation of prevention of islet allograft rejection by ingested IFN-α in the pig, a large animal model suitable for preclinical studies, would provide data leading to human allograft islet transplant trials.

EXAMPLE 2
Alloigraft Islet Transplantation

Allogeneic islet donors (female Yorkshire pigs, 9–12 months old, 50–60 kg bw) are acquired from Charles River [94]. Selection of older donors significantly improves pig islet isolation yield [103]. Islet recipients are micropigs Yucatan (2–4 months old, 6–14 kg body weight) purchased from Charles River. All experimental pigs are kept in the UT animal house and fed commercial chow twice a day. A central catheter is placed in the internal jugular under general anesthesia for STZ and glucose administration. In the recipients, normoglycemia is confirmed and diabetes is induced by injection of intravenous STZ at 150–200 mg/kg bw in 50 ml saline over 2 minutes after fasting of animals [104–106]. Pigs are continuously monitored for 3 hours after STZ administration because vomiting and diarrhea can occur in up to 90% of pigs. If necessary, 250 ml of 50% glucose solution is infused for temporary hypoglycemia for the first 24 hours. Thereafter, serum glucose is determined daily and DM established by at least two daily consecutive FBS>300 mg/dl. Insulin is given s.c. to cover elevated BS to maintain good general condition. Transplant will occur approximately 7 days after STZ administration. Alternatively, total pancreatectomy can be performed to induce DM [94].

EXAMPLE 3
Isolation of Islets and Purification of Porcine Islets

The splenic lobe of the pancreata is intraductally distended with 200 ml of University of Wisconsin solution containing 2.7–3.3 mg/ml collagenase at 4° C. The distended glands are digested in a continuous digestion-filtration device at 32° C. After 60 minutes of cold storage of the pancreatic digest in UW solution, the cleaved islets are purified with a discontinuous iso-osmolar Ficoll-diatrizoate gradient on a Cobe 2991. The purity of the islets is evaluated by dithizone staining. The membrane integrity of the islets is assessed by a fluorescein viability assay. Finally the purified islets are pooled in a RPMI media containing 10% fetal calf serum, glutamine, Hepes, and Pen/strep [94]. Islets are suspended in 100–150 ml of hanks balanced salt solution and infused into the portal vein or a 1–1.5 ml islet suspension injected into the renal subcapsular area once diabetes is established in recipients (approximately 7 days).

Recipients are mock gavaged or gavaged with universal IFN-A/D at 5,000 10,000, 20,000, 30,000, 50,000, 100,000 units/kg daily starting at the time of STZ treatment and daily thereafter. Universal Type I Interferon, also called human interferon alpha A/D, is an alpha interferon hybrid that crosses the species barrier and is constructed from the recombinant human interferons-αA and -αD. Universal Type I Interferon has been proven active on virtually every mammalian cell. It can substitute for any human, monkey, mouse, bovine, rat, cat, dog, rabbit, sheep, goat, horse, pig or hamster type I interferon (alpha, beta, omega, and tau). Universal Type I Interferon has proven to be valuable as a less expensive alternative or as a substitute for unavailable interferons, allowing experiments that might not otherwise be possible. Alternatively human recombinant IFN-α (Roferon) can be used, transpecies-effective in mice and rats [11, 12]. BS is checked daily and if elevated >300 mg/dl, FBS will be checked to determine if rejection has occurred, rejection indicated by two consecutive FBS>300 mg/dl.

EXAMPLE 4
Statistics

Figure 2:
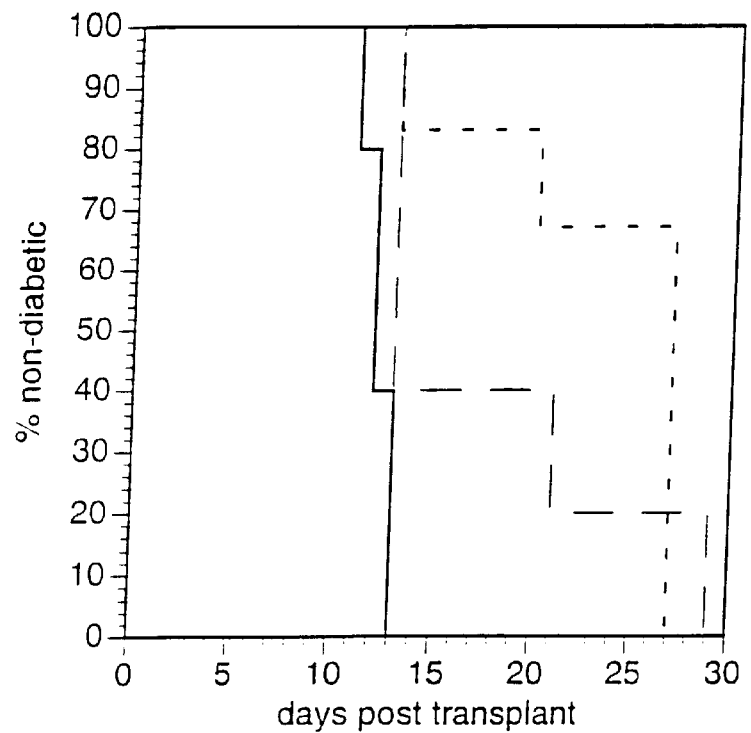
FIG. 2 shows that ingested IFN-α delays rejection of allograft islet transplants in mice.
Figure 3:
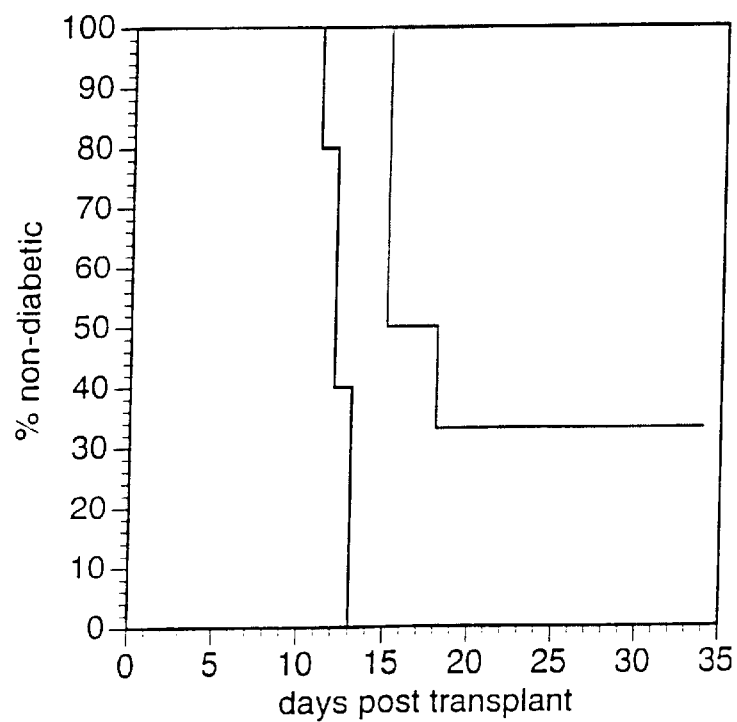
FIG. 3 shows that continuous ingested IFN-α prolongs allograft islet transplant survival.

The data shows that 21 days of ingested IFN-α doubled graft survival in mice from 13 days to 28 days FIG. 2. For purposes of analysis, under the assumption of a doubling of graft survival in pigs with the appropriate dose of ingested IFN, 5 pigs per group (SigmaStat, sample size for mouse experiments, mean control 12.2 days, mean 100U 23.5 days, SD 5.85, with $\alpha=0.05$ and $\beta=0.8$) were needed. To do dose-ranging experiments with at least 4 different doses of IFN-α (500, 5,000, 20,000, and 50,000/kg) and control (n=25), and repeat successful experiments three times, then 85 recipients are necessary. Two donors are estimated to be needed for each recipient.

EXAMPLE 5
Vertebrate Animals 165 yorkshire donor pigs and 85 micropig yucatan recipients are used during the grant period, 2 donors for each recipient pigs. Yorkshire pigs provide potential large amounts of allograft islets and Yucatan minipigs recipients are smaller, probably require less transferred islets for normoglycemia, and are easier to care for and should be suitable for transfer experiments. Pigs are euthanized via IV telazol 4 mg/kg followed by buthanasia 0.22 ml/kg.

EXAMPLE 6
Results

It has been demonstrated that ingested IFN-α prevents type I diabetes in the NOD mouse and prolongs the "honeymoon"period in newly diagnosed type I diabetics. In order to examine the mechanism of protection against rejection of ingested IFN-α, it must be determined if T cell subsets have different potentials in transferring type I diabetes, define the best dose of diabetic (DM) cells for the experimental model, and establish that donor IFN-fed transferred cells may protect against type I diabetes in the NOD.scid platform. In the first experiment, it is demonstrated that type I diabetes were transferred to NOD.scid mice (Table 1). Splenocytes, purified T, CD4+ and CD8+ T splenic cells were transferred from diabetic NOD mice into NOD.scid mice and determined blood glucoses (# diabetic mice/total # recipients). Splenocytes, T cells and CD8+ T cells were able to transfer type I diabetes over 4–8 weeks. I n contrast, only 2/3 mice receiving CD4+ T cells from diabetic donors transferred type I diabetes after 16 weeks. CD4+ T cells are significantly different in their ability to transfer disease and may be protective in the experimental model.

Next to be established is the dose of diabetogenic splenocytes that would transfer type I diabetes over a gradual period allowing prediction of impending overt diabetes (Table 2). Four groups of 2 mice each were injected with "diabetic" whole splenocytes i.p. and followed for BS>200 mg/ml. Group 1 received $10\times10^6$, group 2 received $3\times10^6$, group 3 received $1\times10^6$, and group 4 received $0.3\times10^6$ DM splenocytes. This data below demonstrates that as little 300,000 "diabetic" cells can transfer type I diabetes into NOD.scid recipients. The tempo of NOD.scid diabetes was directly related to the number of transferred cells. NOD.scid BS tend to very low without diabetic cells. This data suggests that NOD. scid BS>100 predict impending type I diabetes in group 4. The $0.3\times10^6$ transfer gave the slowest onset of type I diabetes, and therefore allows the best predictability of possible impending islet allograft rejection in comparable experiments using syngeneic 'rejector' cells.

TABLE 1

Splenocytes, T cells and CD8+ T cells transfer DM to NOD.scid better than CD4+ T cells

| #cells transferred | Weeks Post Transfer | | | | |
|---|---|---|---|---|---|
| | 4 | 5 | 6 | 8 | 12 | 16 |
| $10^7$ splenocytes | — | — | 2/4 | 3/4 | 4/4 | — |
| $15 \times 10^6$ T | 4/4 | — | 4/4 | 4/4 | — | — |
| $6 \times 10^6$ CD8+ T | 2/3 | 3/3 | — | — | — | — |
| $6 \times 10^6$ CD4+ T | 0/3 | 0/3 | 0/3 | 0/3 | 1/3 | 2/3 |

TABLE 2

Dose-response effect of diabetogenic cells on the incidence of DM in NOD.scid mice

| | week 3 | week 4 | week 5 | week 6 | week 7 | week 8 | week 9 | week 10 | week 11 | week 12 | week 13 |
|---|---|---|---|---|---|---|---|---|---|---|---|
| $10 \times 10^6$ | 102 | 600 | dead | dead | dead | dead | dead | dead | dead | dead | dead |
| | 95 | 600 | 600 | dead | dead | dead | dead | dead | dead | dead | dead |
| $3 \times 10^6$ | 73 | 600 | 600 | 600 | 600 | 600 | dead | dead | dead | dead | dead |
| | 116 | 79 | 84 | dead | dead | dead | dead | dead | dead | dead | dead |
| $1 \times 10^6$ | 76 | 79 | 600 | 600 | dead | dead | dead | dead | dead | dead | dead |
| | 62 | 90 | 364 | 600 | 600 | dead | dead | dead | dead | dead | dead |
| $0.3 \times 10^6$ | 52 | 88 | 112 | 600 | 600 | 600 | dead | dead | dead | dead | dead |
| | 77 | 92 | 98 | 121 | 342 | 600 | 600 | 600 | 600 | 600 | dead |

Next to be examined is whether transferred CD4+ T cells from type I IFN-fed donors, a T cell subset known to be protective in the NOD mouse, protected against overt type I diabetes in NOD.scid recipients of diabetic splenocytes (Table 3). NOD.scid mice received 3,000 "diabetic" splenocytes at week 0 (control) or 300,000 diabetic cells and concurrently $3\times10^6$, $1\times10^6$, or $0.3\times10^6$ IFN-α-fed splenic purified CD4+ T cells (>90% pure) from IFN-α-fed donors i.p. and followed for overt DM. Donor mice had been fed for 8 consecutive weeks with 100 U mIFN-α. The results in Table 3 suggest that 3 million CD4+ T cells from IFN-a-fed donors may be protective. Higher quantities of CD4+ T cells may provide additional protection. This data provides the framework for further work using "rejector" T cells and protective IFN-fed CD4+ T cell populations from spleen or GALT.

TABLE 3

CD4+ T cells from type I IFN-fed donors may protect against adoptive transfer of DM into NOD. scid recipients.

| | 2 wk | 3 wk | 4 wk | 5 wk | 6 wk | 7 wk | 8 wk | 9 wk | 10 wk | 11 wk | 12 wk | 13 wk |
|---|---|---|---|---|---|---|---|---|---|---|---|---|
| 3M | 69 | 73 | 100 | 77 | 102 | 122 | 92 | 97 | 104 | 100 | 106 | 115 |
| | 71 | 82 | 96 | 88 | 103 | 135 | 96 | 100 | 112 | 111 | 80 | 121 |
| 1M | 78 | 69 | 88 | 92 | 102 | 192 | 383 | 600 | 600 | 600 | 600 | 600 |
| | 55 | 57 | 93 | 88 | 91 | 99 | 117 | 162 | 600 | 600 | 600 | 600 |
| 300K | 81 | 88 | 87 | 151 | 93 | 187 | 110 | 417 | 600 | 600 | dead | dead |
| | 73 | 91 | 82 | 100 | 140 | 110 | 600 | 600 | 600 | 600 | 600 | 600 |
| ctr | 65 | 83 | 115 | 122 | 93 | 147 | 347 | 600 | dead | dead | dead | dead |
| | 77 | 80 | 90 | 108 | 105 | 115 | 112 | 133 | 200 | 288 | dead | dead |

EXAMPLE 7

Ingested IFN-α Prolongs the "Honeymoon" Period in Newly Diagnosed Type I Diabetes.

Figure 1B:
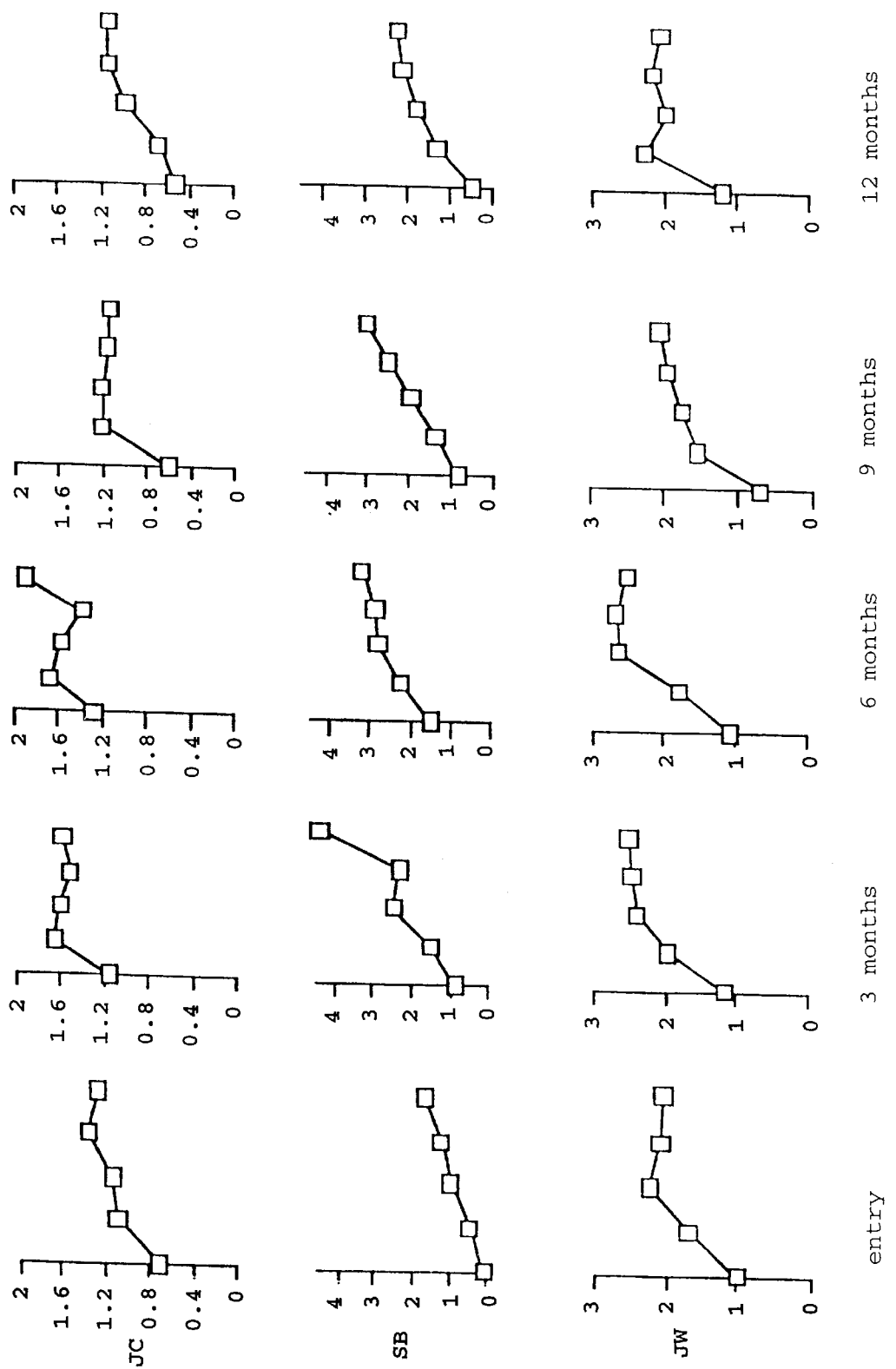

The understanding of the protective mechanism of ingested IFN-α in the NOD mouse model is important because of the findings in newly diagnosed type I diabetes patients. The efficacy and toxicity was examined of ingested hrIFN-α in prolonging or maintaining the "honeymoon" period of newly diagnosed type I diabetes (<one month post diagnosis; ADA criteria FBS>125, 2 hour post-prandial >200). Five Caucasian patients less than 25 years old with newly diagnosed type I diabetes were studied within one month of diagnosis in an open label clinical trial of every other day ingestion of 30,000 units hrIFN-α for up to one year (FIGS. 1A and 1B). The primary outcome measure was a 30% increase of stimulated C-peptide levels after Sustacal® administration at 0, 3, 6, 9, and 12 months. All patients were on insulin and had metabolically well-controlled diabetes. As a condition of entry into the study, the patient agreed to check capillary glucose before each meal and at bedtime every day, at 3 a.m. once a fortnight with review of the results with endocrinologist at least every 2 weeks to attain certain levels of BS control. The blood sugars of the patients were well controlled according to ADA standards of serum levels 80–120 before meals, 100–140 at bedtime. The Sustacal® tolerance test, a standardized test for residual insulin secretion, was performed as follows: Patients followed a high CHO diet for three days before the test and used regular insulin the evening before the test. After an overnight fast (post 10:00 PM the night before the test), glucose/C-peptide was drawn fasting. Subjects ingested Sustacal® at 7 cc/kg (max 400 cc) over five minutes. Serum for glucose and C-peptide determinations was obtained at 30, 60, 90 and 120 minutes post Sustacal®. Sustacal ingestion generated a hyperglycemic response in all patients. Compliance was >90% in all cases confirmed by patients logs in the Clinical Research Center chart.

Three of the first five patients demonstrated biochemical "honeymoon" of at least a 30% increase of stimulated C-peptide levels at 0, 3, 6, 9 and 12 months after initiation of ingested IFN-α (FIGS. 1A and 1B). There were no discernible chemical or clinical toxicities associated with ingested IFN-α therapy in this first group of patients.

Figure 1C:
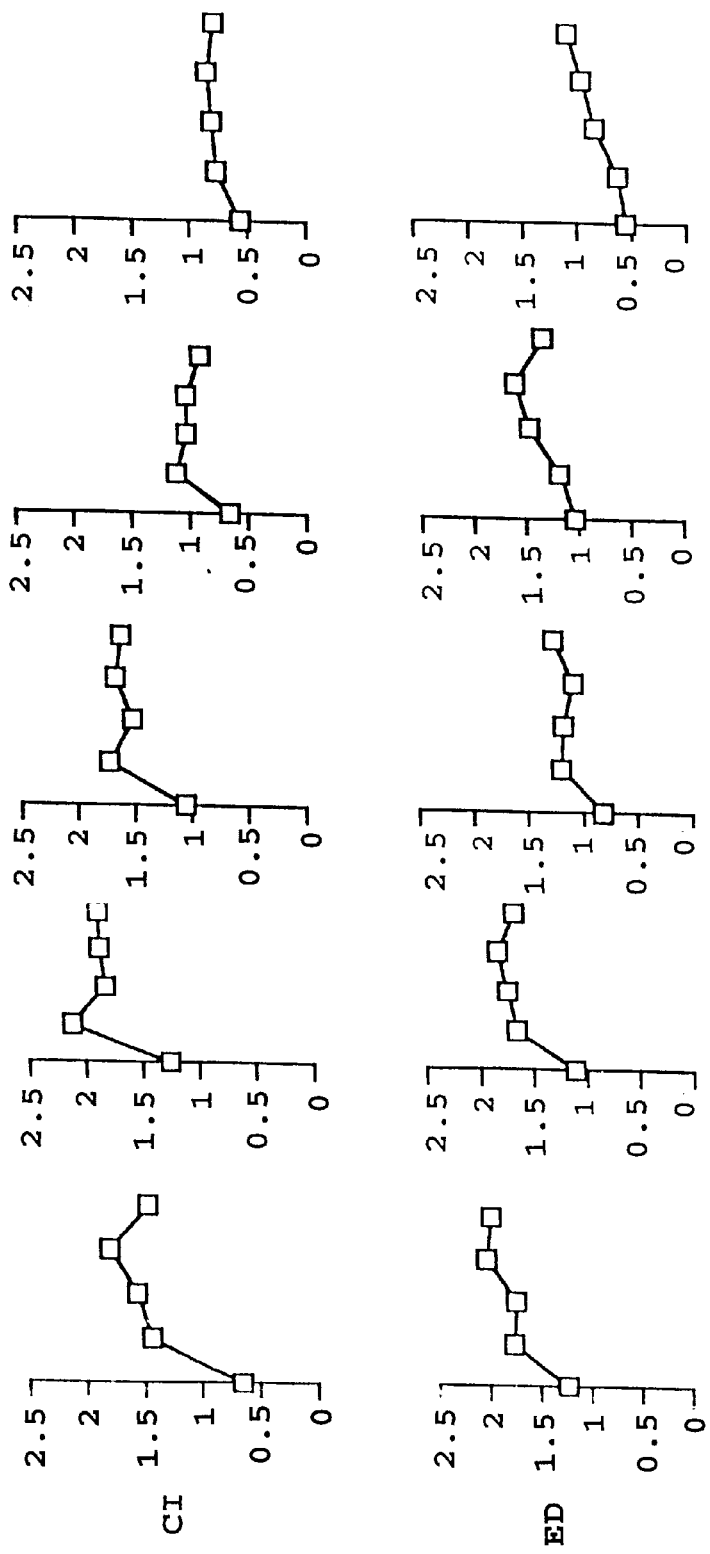
FIGS. 1C and 1D show that every day ingested IFN-α prolongs the "honeymoon" period in newly diagnosed IDDM.
Figure 1D:
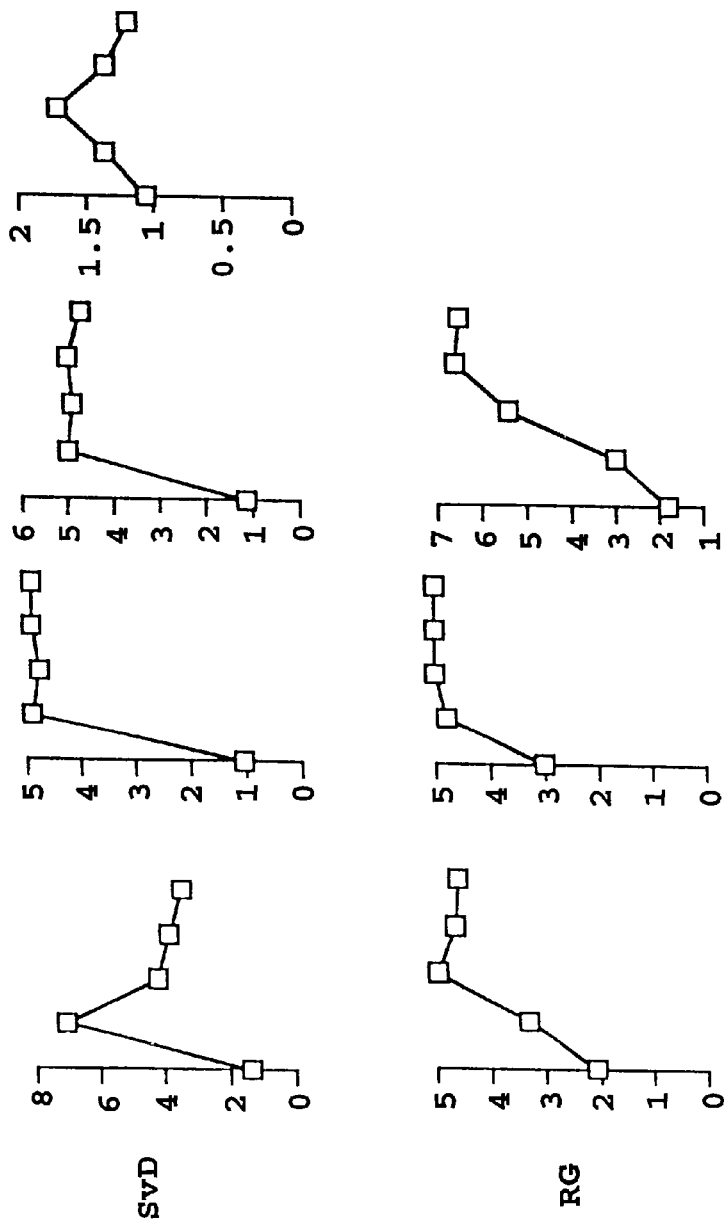

There was a second group of four patients, similar to the first five type I diabetes patients, placed on every day dosing of 30,000 units ingested IFN-α (FIGS. 1C and 1D). Every day dosing was used because daily dosing of ingested IFN-α was the most effective in delaying the onset of diabetes in NOD mice. All four patients remain in honeymoon at the present time after 12, 12, 9 and 6 months, respectively. Therefore, in the 7 patients that have completed the trial up to the present time, 5/7 remained in honeymoon for at least 12 months. The remaining patients will be followed with Sustacal induced c-peptide assessments for 12 months. This data indicates that ingested IFN-α has potential as a therapeutic agent in newly diagnosed type I diabetes and in patients at "high risk" of developing type I diabetes as prevention.

Discussion

Type I IFNs may be the critical anti-inflammatory cytokines counteracting pro-inflammatory IFN-γ in type I diabetes and transplant rejection [72]. A unifying hypothesis is proposed of the etiopathogenesis of type I diabetes that defines type I diabetes as a type I IFN immunodeficiency syndrome. At the core of the unifying theory is the interaction between the two major components of the immune system, the older innate and the newer acquired immune systems. Foreign nucleic acids, cells, and bacteria cause type I IFN secretion by the innate immune system and acts as the initial nonspecific antiviral, antibacterial and antiproliferative defense system. Type I IFN secretion activates antigen presenting cells allowing the transition into the antigen-specific humoral and cell-mediated immunity. However, the products of the innate immune system, type I IFNs, can also function as immunomodulators to balance the effects of the acquired immune system. It is hypothesized that under normal circumstances there is a dynamic interaction between the innate immune system that initially generates anti-foreign and secondarily immunomodulating cytokines including IFN-α/β (type I IFNs) and the acquired immune system that generates pro-inflammatory IFN-γ (type II IFN), resulting in a physiological downmodulation of the total immune response. In DM and possibly in other autoimmune diseases, there may be a deficiency of immunomodulation of the innate immune system.

Is there in vitro evidence that pro-inflammatory IFN-γ can induce counterregulating IFN-α/β? IFN-γ enhances the production of in vitro Sendai virus-induced IFN-α in human monocytesimacrophages that are efficient producers of IFN-α [73]. In vitro experiments demonstrate that not only is the major antiviral mechanism of IFN-γ acting through IFN-α in mice but that IFN-γ can negatively regulate its own effects via IFN-α [74]. The above demonstrates that in in vitro systems IFN-γ can downregulate its own activity by inducing a counterregulatory IFN-α/β response.

Is there direct in vivo evidence in animal models that type I IFNs, in particular IFN-α, counteract pro-inflammatory IFN-γ? During infections in mice with murine cytomegalovirus (MCMV), there is increased IFN-α/β expression. Neutralization of IFN-α/β in MCMV infected mice increases early IFN-γ protein production. Furthermore, during infections of mice with lymphocytic choriomeningitis virus (LCMV), blocking IFN-α/β activity revealed a previously undetected early IFN-γ protein expression. The effects of IFN-α/β neutralization on production of IFN-γ during the viral infections were detected in both serum samples and medium conditioned with splenic leukocytes isolated from infected animals. These results demonstrate a new mechanism for inhibition of IFN-γ immune responses in vivo [75]. IFN-γ and IFN-α/β possess opposite activities in vivo, IFN-α modulating the immunity of IFN-γ. It is hypothesized that anti-inflammatory cytokines including IFN-a/p, produced by adoptively transferred protective cells, will counterregulate pro-inflammatory cytokines, especially IFN-γ at the site of inflammation (allograft) and inhibit rejection.

If type I IFNs are immunomodulatory and capable of regulating the immunity generated by IFN-γ, how do type I IFNs perform this function effectively? T cell proliferation in vivo is presumed to reflect a TCR-mediated polyclonal response directed to various environmental antigens. However, the primary immune response to allografts is often intense. The activation of antigen-specific T cells suggests that a substantial component of the T cell proliferative response is not antigen-specific. The massive proliferation of T cells seen in viral rejection is suggestive of a bystander reaction driven by cytokines instead of the TCR. In mice, T cell proliferation preferentially affects T cells and is mimicked by injection of poly(I:C), an inducer of type I IFN, and also by purified type I IFNs; such proliferation was not associated with up-regulation of CD69 or CD25 expression but upregulation of Ly-6C, a marker of IFN activation. This implies that TCR signaling is not involved.

Therefore, stimulation of T cells does not seem to require TIR ligation, appears after interaction with type I IFN, and therefore provides a pathway for regulation of inflammation [76, 77].

The following references were cited herewith.

1. Foulis et al., Diabetologia 1986; 29(5): 267–74.
2. Serreze et al., Curr Opin Immunol 1994; 6: 900–906.
3. Hanafusa et al., Diab Res Clin Prac 1994; 24 Suppl: S307–311.
4. Wicker et al., Annu Rev Immunol 1995; 13: 179–200.
5. Atkinson et al., Sci Am 1990; 263(1): 62–3, 66–71.
6. Castano et al., Annu Rev Immunol 1990; 1 8: 647–679.
7. LaFace et al., Diabetes 1989; 38(7): 894–901.
8. Lampeter et al., Lancet 1993; 341: 1243–1244.
9. Leiter et al., Reg Immunology 1993; 4: 263–273.
10. Brod et al., Neurology 1994; 44(6): 1144–8.
11. Brod et al., J Neuroimmunol 1995; 58(1): 61–9.
12. Brod et al., J Interferon Cytokine Res 1995; 15(2): 115–22.
13. Brod,*Interferon Therapy in Multiple Sclerosis,* A. T. Reder, Editor. 1996, Marcel Dekker.
14. Brod et al., J Autoimmun 1996; 9(1): 11–20.
15. Brod et al.,. J Int Cyt Res 1997; 17(supplement 2): S87.
16. Brod et al., Diabetologia 1998; 41: 1227–1232.
17. Healey et al., J Clin Invest 1995; 95: 2979–2985.
18. Foulis et al., J Pathol 1991; 164: 97–103.

19. Campbell et al., J Autoimmunity 1991; 4: 237–248.
21. Nicoletti et al., Lancet 1990; 336: 319.
22. Sarvetnick et al., Cell 1988; 52: 773–782.
23. Sarvetnick et al., Nature 1990; 346: 844–847.
24. Ablamunits et al., J Autoimmun 1998; 11(1): 73–81.
25. Zekzer et al., J Clin Invest 1998; 101(1): 68–73.
26. Foulis, Diabetologia 1996; 39: 127.
27. Huang et al., Diabetes 1995; 44(6): 658–64.
28. Stewart et al., Science 1993; 260(5116): 1942–6.
29. Huang et al., Immunity 1994; 1: 469–478.
30. Serreze et al., J Autoimmunity 1989; 2: 759–776.
31. Sobel et al., J Autoimmun 1998; 11(4): 343–52.
32. Sobel et al., Diabetes 1998; 47(12): 1867–72.
33. Faust et al., Transplantation 1996; 62(5): 648–52.
34. Rapoport et al., J Exp Med 1993; 178(1): 87–89.
35. Mueller et al., J Exp Med 1996; 184(3): 1093–1099.
36. Berman et al., J Immunol 1996; 157(10): 4690–6.
37. Pennline et al., Clin Immunol Immunopath 1993; 71: 169–175.
38. Zheng et al., J Immunol 1997; 158(9): 4507–13.
39. Kaser et al., Cytokine 1998; 10(2): 75–81.
40. Aman et al., Blood 1996; 87(11): 4731–6.
41. Schandene et al., J Clin Invest 1996; 97(2): 309–15.
42. Wong et al., J Exp Med 1996; 183: 67–76.
43. Rohane et al., Diabetes 1995; 44: 550–554.
44. Christianson et al., Diabetes 1993; 42: 44–55.
45. Akhtar et al., J Exp Med 1995; 182: 87–97.
46. Prochazka et al., Proc Natl Acad Sci USA 1992; 89: 3290–3294.
47. Nerup et al., Diabetologia 1994; 37 (suppl 2): S82–89.
48. Kovarik et al., Immunol Cell Biol 1997; 75(3): 303–9.
49. Rabinovitch et al., Diabetologia 1994; 37(8): 833–7.
50. Li et al., J Immunol 1998; 161(5): 2241–7.
51. Stephens et al., Journal of Autoimmunity 1997; 10(3): 293–8.
52. Nickerson et al., Transplant Proc 1993; 25(1 Pt 2): 984–5.
53. Kovarik et al., Transpl Immunol 1997; 5(4): 307–14.
54. Ozasa et al., Transplantation 1997; 64(8): 1152–9.
55. Katz et al., Transplant Proc 1997; 29(1–2): 748–9.
56. Renz et al., J Surg Res 1996; 65(1): 34–41.
57. Isaacs et al., Proc R Soc Lond [Biol] 1957; 147: 258–267.
58. Dron et al., *Interferon α/β, gene structure and regulation*, in *Interferon—Principles and Medical Applications*, 1992, UTMB Press: Galveston, Tex. p. 33–46.
59. Uze et al., J Interferon Cyt Res 1995; 15: 3–26.
60. Pfeffer et al., Cancer Research 1990; 50: 2654–2657.
61. Pfeffer et al., Pharmac Ther 1991; 52: 149–151.
62. Horisberger M A. *Mx protein: Function and mechanism of action*, in *Interferon: Principles and medical applications*, 1992, UT Press: Galveston, Tex. p. pp 215–224.
63. Brod S. *Effect of oral administration of type 1 interferon on experimental autoimmune encephalomyelitis*, in *Interferon Therapy in Multiple Sclerosis*, 1997, Marcel Dekker, Inc.: New York Basel Hong Kong. p. 245–286.
64. Brod et al., Mult Scler 1997; 3(1): 1–7.
65. Fleischmann et al., Proc Soc Exp Biol Med 1992; 201(2): 200–7.
66. Cantell et al., J Gen Virol 1973; 20: 97–104.
67. Gibson et al., J Interferon Res 1985; 5: 403–408.
68. Wills et al., J Interferon Res 1984; 4: 399–409.
69. Witt et al., J Interferon Res 1992; 12: 411–413.
70. Roers et al., J Infect Dis 1994; 169(4): 807–13.
71. Brod et al., Cytokine 1998; in press.
72. Brod et al., J Interferon Cyt Res 1996; 16(6): 461–3.
74. Hughes et al., J Biol Reg & Homeo Agents 1987; 1(1): 29–32.
75. Cousens et al., Proc Nat Acad Sci USA 1997; 97(2): 634–9.
76. Sprent et al., Immunol Rev 1997; 156: 79–85.
77. Tough et al., Science 1996; 272(5270): 1947–50.
78. Brandtzaeg et al., Curr Topics Microbiol Immunol 1989; 146: 13–28.
79. Witmer et al., Am J Anat 1984; 170: 465–481.
80. Ermak et al., Immunology 1990; 71: 530–537.
81. MacDonald et al., Eur J Immunol 1983; 13(2): 138–42.
82. Santos et al., Cell Immunol 1994; 157(2): 439–47.
83. Ford et al., Semin Hematol 1969; 6: 67–83.
84. Blalock et al., Nature 1977; 269: 422–425.
85. Butcher, Curr Topics Microbiol Immunol 1986; 128: 85–122.
86. Bocci, Immunology 1988; 64: 1–9.
87. Butcher et al., Science 1996; 272 (5 April): 60–66.
88. Bretzel et al., Exp Clin Endocrinol Diabetes 1995; 103 Suppl 2: 143–59.
89. Kendall et al., Diabetes Metab 1996; 22(3): 157–63.
90. Casteels et al., Transplantation 1998; 65(9): 1225–32.
91. Morel et al., Transplant Proc 1992; 24(3): 1048–50.
92. Tuch et al., Transplant Proc 1995; 27(6): 3375.
93. Sandberg et al., Transplantation 1996; 61(8): 1211–5.
94. Mellert et al., Transplantation 1998; 66(2): 200–4.
95. Ueki et al., Diabetes Res Clin Pract 1993; 20(1): 11–9.
96. Ochiai et al., Transplant Proc 1998; 30(2): 663.
97. Wahoff et al., Transplant Proc 1996; 28(2): 912.
98. Tufveson et al., Transplant Proc 1994; 26(5): 3029–39.
99. Guo et al., Transplantation 1998; 65(10): 1310–4.
100. Koulmanda et al., Transplant Proc 1997; 29(4): 2161–2.
101. Hao et al., Transplant Proc 1992; 24(6): 2843–4.
102. Weir et al., *Islet isolation from rodent pancreas*, in *Procurement of pancreatic Islets* 1994, RG Landes: Austin. p. 53–69.
103. Socci et al., Horm Metab Res Suppl 1990; 25: 32–4.
104. Liu et al., Transplant Proc 1998; 30(2): 574–5.
105. Wilson et al., Aust J Exp Biol Med Sci 1986; 64(Pt 6): 489–500.
106. Grussner et al., Horm Metab Res 1993; 25(4): 199–203.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting transplant rejection in an animal, comprising the step of:

orally administering a type one interferon to said animal, wherein said type one interferon is ingested after oral administration.

2. The method of claim 1, wherein said interferon is selected from the group consisting of alpha-interferon and beta-interferon.

3. The method of claim 2, wherein said interferon is selected from the group consisting of human recombinant interferon, rat interferon and murine interferon.

4. The method of claim 2, wherein said interferon is administered in a dosage of from about 50 I.U./kg to about 50,000 I.U./kg.

5. The method of claim 1, wherein said interferon is administered every other day.

6. The method of claim 1, wherein said interferon is administered daily.

7. The method of claim 1, wherein said animal is selected from the group consisting of mouse, pig, rat and human.

8. The method of claim 1, wherein said transplant is islet allograft transplant.

* * * * *

UNITED STATES PATENT AND TRADEMARK OFFICE
CERTIFICATE OF CORRECTION

PATENT NO. : 6,346,243 B1
DATED : February 12, 2002
INVENTOR(S) : Staley A. Brod It is certified that error appears in the above-identified patent and that said Letters Patent is hereby corrected as shown below:

Column 2,
Line 36, "0-cells" should read -- B-cells --.

Column 3,
Line 8, "arkers" should read -- Markers --.
Line 14, "CD14+" should read -- CD4+ --.

Column 5,
Line 36, "mRNAlprotein" should read -- mRNA protein --.
Line 46, "spelnocytes" should read -- splenocytes --.
Line 61, "nOD" should read -- NOD --.

Column 6,
Line 16, "IFN-αmay" should read -- IFN-α may --.
Line 41, "An representative" should read -- A representative --.
Line 57, "are" should read -- is --.

Column 8,
Line 4, please insert parentheses around "FIG. 2".
Line 21, "pigs" should read -- pig --.
Line 41, "were" should read -- was --.
Line 46, please delete the space in "I n".

Column 10,
Line 4, "was" should read -- were --.
Line 40, please delete the space in "a s".
Line 66, "patients" should read -- patients' --.

Column 11,
Line 34, "acts" should read -- act --.
Line 56, "monocytesimacrophages" should read -- monocytes/macrophages --.

Column 12,
Line 11, please change the period after "vivo" to a comma.
Line 13, "IFN-a/p" should read -- IFN--α/β --.
Line 38, "TIR" should read -- TCR --.

UNITED STATES PATENT AND TRADEMARK OFFICE
CERTIFICATE OF CORRECTION

PATENT NO.    : 6,346,243 B1
DATED         : February 12, 2002
INVENTOR(S)   : Staley A. Brod It is certified that error appears in the above-identified patent and that said Letters Patent is hereby corrected as shown below:

Column 15,
Line 3, please delete the space in "th e".

Signed and Sealed this

Fourth Day of February, 2003

JAMES E. ROGAN
*Director of the United States Patent and Trademark Office*